United States Patent [19]
Steer et al.

[11] Patent Number: 5,593,396
[45] Date of Patent: Jan. 14, 1997

[54] BAG FOR CONTAINING LIQUID

[75] Inventors: Peter L. Steer, Kingscote; Graham E. Steer, London; John A. Gent, Liphook, all of United Kingdom

[73] Assignee: E. R. Squibb & Sons, Inc., Princeton, N.J.

[21] Appl. No.: 214,893

[22] Filed: Mar. 17, 1994

[30]  Foreign Application Priority Data

Mar. 18, 1993 [GB] United Kingdom ............... 9305558
Feb. 15, 1994 [GB] United Kingdom ............... 9402876

[51] Int. Cl.$^6$ .................................................. A61M 1/00
[52] U.S. Cl. .................... 604/327; 128/DIG. 24; 604/332; 604/340; 206/524.8; 383/904
[58] Field of Search .................... 128/DIG. 24; 604/323, 604/327, 328, 329, 332, 335, 337, 408; 383/77, 904; 206/524.8

[56]  References Cited

U.S. PATENT DOCUMENTS

| | | | |
|---|---|---|---|
| 3,009,498 | 11/1961 | Fohr ......................................... | 383/904 |
| 4,257,535 | 3/1981 | Mellett ........................... | 128/DIG. 24 |
| 4,295,566 | 10/1981 | Vince .................................... | 206/524.8 |
| 5,536,469 | 7/1996 | Jonsson et al. ......................... | 604/408 |

*Primary Examiner*—John G. Weiss
*Assistant Examiner*—Mark O. Polutta
*Attorney, Agent, or Firm*—Stuart E. Krieger

[57]  ABSTRACT

A combination of a liquid-containing bag and a tube 28 is disclosed. The bag may be a urine drainage bag and is made up of a pair of superposed sheets 20, 22, joined by a weld 24 whose configuration is chosen to define in a single welding operation the outline of the bag and the tube integral therewith. A single weld seam 24 defines the bag volume. The tube and portion of the weld seam 24 run adjacent to one another and are separated by a row of perforations 30 or by a line of weakening. In such an arrangement, means are provided for precluding face-to-face contact of selected parts of the inner surfaces of said sheets. This may be done by effecting heat shrinkage of selected parts of one or both sheets. One or preferably both sheets is biaxially oriented.

7 Claims, 2 Drawing Sheets

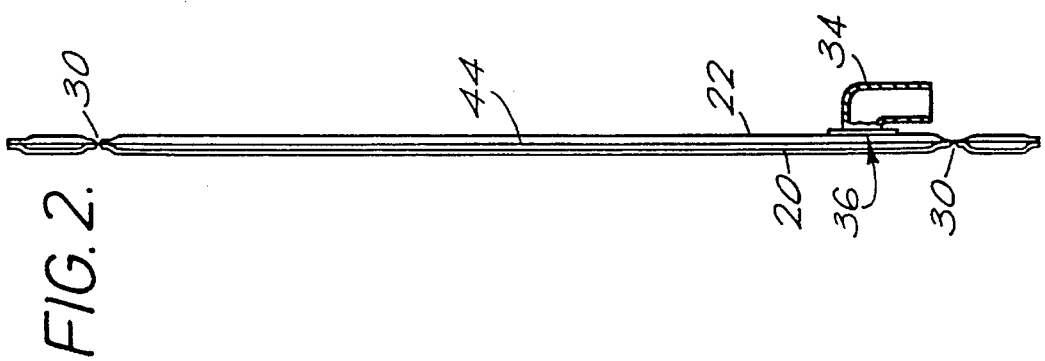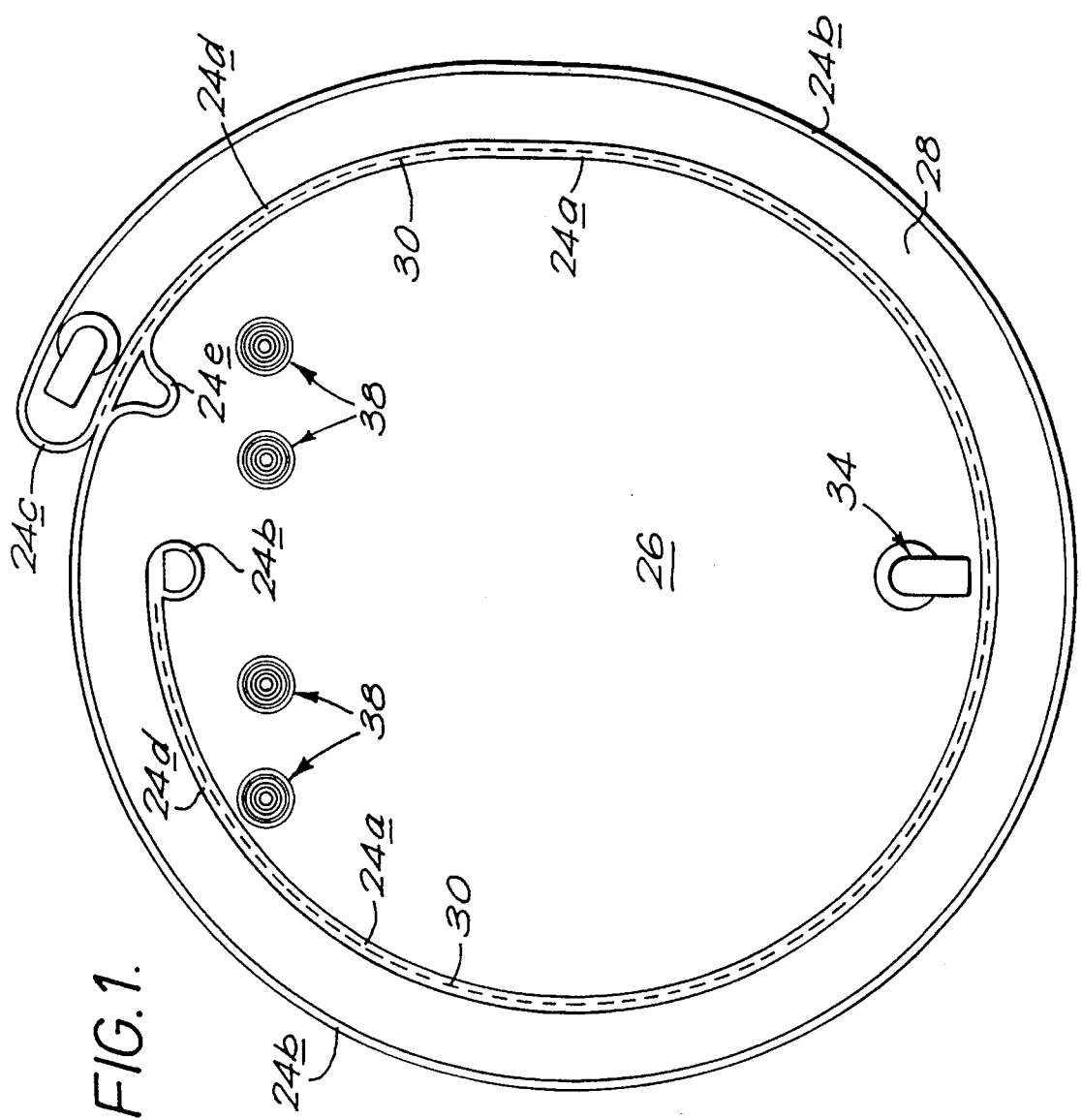

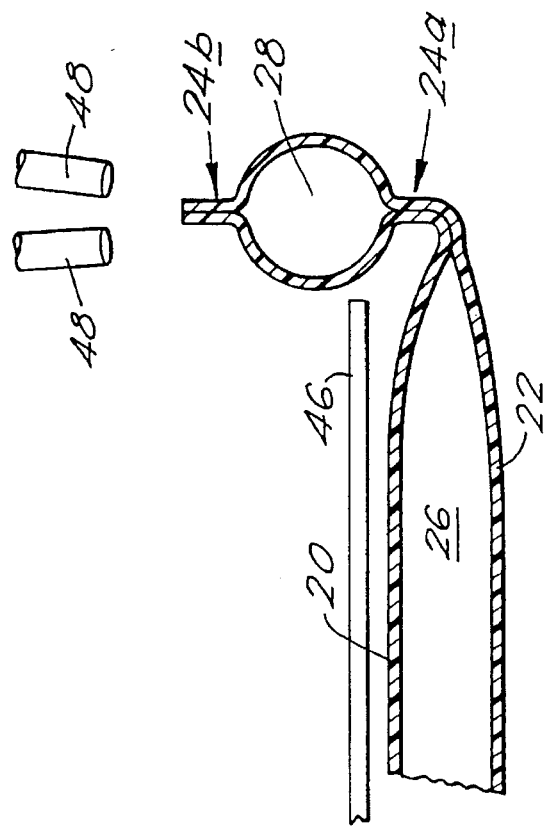
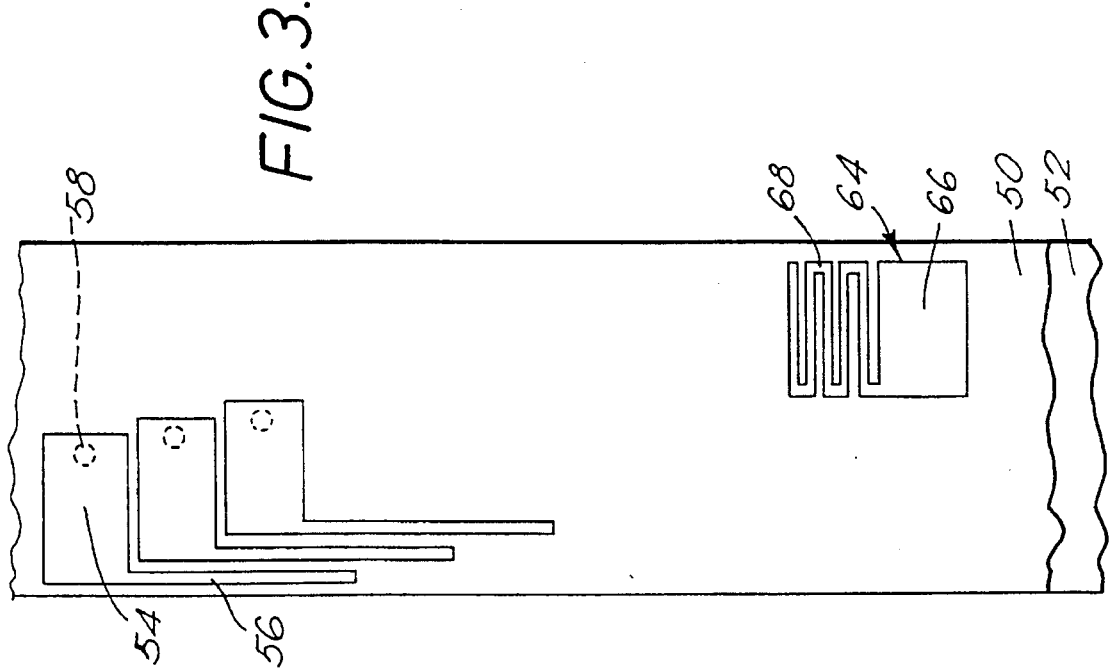

5,593,396

BAG FOR CONTAINING LIQUID

BACKGROUND OF THE INVENTION

This invention relates to a bag, for supplying or receiving a liquid to or from a person. In particular, the invention relates to leg bags, urine drainage bags, and fluid delivery bags for blood supply or parenteral feeding bags, but may also relate to bags or pouches for other purposes, e.g. solution bags for I.V. sets.

Liquid containing bags are normally made from two sheets of plastics film-like material welded together around their periphery. Efforts have been made, see for example U.K. Patents Nos. 2,203,125; 2,197,849 and 2,206,169 to attach tubes to bags in a satisfactory way. There remains, however, a need for an easily-manufactured bag in which the possibility of leakage is reduced virtually to zero.

A device collection urine from an incontinent patient is disclosed in U.S. Pat. No. 4,559,049. The device includes a bag integral with an inlet duct. The inlet duct extends between an inlet valve and the bag and is made of two synthetic foil portions, the peripheral strips whereof are welded together, and one of them is then subjected to thermal shrinkage. In this way, the duct is kept open.

OBJECTS AND SUMMARY OF THE INVENTION

According to the present invention, there is provided a bag and tube combination comprising a pair of superposed sheets, joined by a weld whose configuration is chosen to define in a single welding operation the outline of the bag and the tube integral therewith, in which means are provided for precluding face-to-face contact of selected parts of the inner surfaces of said sheets, and in which a single weld seam is employed to define the bag volume and the tube end portions of said seam run adjacent to one another and side by side, having between them a line of weakening, e.g. a row of perforations.

According to one embodiment of the present invention there is provided a bag made from two superposed plastics sheets, the sheets being welded together in such a way as to define by a single weld seam a bag volume and a tube which is in communication with the bag volume, one of said sheets being of a biaxially oriented plastics material and the other being conventional 'relaxed' plastics sheet.

In this specification, the term 'relaxed' as applied to a plastics sheet means relieved of internal stress induced by mechanical or other means, i.e. in its normal state as manufactured.

In the said embodiment version of the invention, the tube is defined by two end portions of the said weld, said portions being generally parallel, the configuration being such that the tube partially surrounds the bag volume.

In one embodiment of the invention, one of the two sheets welded together is biaxially oriented polymer made by a known static process [e.g. mechanical stretching] and the other sheet is a normal relaxed plastics film. In manufacture, the two sheets are welded together to form the product profile and then passed under a radiating heat source, e.g. an infra red radiation source, thus shrinking the biaxially oriented sheet and creating crinkles and irregularities therein.

As a consequence of these crinkles and irregularities in one of the plastics sheets, the tendency for the two plastics strips defining the tube to stick together is greatly reduced.

Hence it is possible for urine or other liquid to pass easily through the tube, and it is easier for the bag volume to expand and fill because the crinkles and irregularities ensure that the two sheets are not in face-to-face contact all over the bag area.

Eyelets produced by plastics RF or heat welding are preferably included, within the weld seam portion which defines the bag volume.

In a presently-preferred embodiment of the invention, the bag and tube combination is made from two substantially identical heat-shrinkable films, that is to say, films possessing substantially the same heat shrink characteristics. In manufacture, during the heat shrinkage step, it is desirable to supply air at low pressure to the space between the films being joined. By 'low pressure' in this context is meant air at a pressure within the range about 1 to about 2 p.s.i.g. It is preferred that the film area which is to form the bag should be protected against the heat, e.g. by an insulating board of corresponding shape, and it is also desirable that the portion of the films which is to form the tube is subjected to hot air shrinkage from above. A consequence of this is that the tubing portion curls upwardly relative to the bag portion.

The invention will be better understood from the following non-limiting description of an example thereof given with reference to the accompanying drawings.

BRIEF DESCRIPTION OF THE DRAWINGS

FIG. 1 is a plan view of one embodiment of the invention;

FIG. 2 is a cross-sectional views on the lines II—II of FIG. 1;

FIG. 3 illustrates an alternative shape for an integral bag and tube which may be used for the rapid manufacture of liquid-containing bags according to the invention; and FIG. 4 diagrammatically illustrates, in cross-section, the way in which the tube portion curls upwardly, relative to the bag portion, in the heat shrinkage step.

DETAILED DESCRIPTION OF THE INVENTION

It will be understood that the invention is not limited to any particular configuration of bag and tube but embodies the concept of providing an integral bag and tube combination by plastics welding of two superposed sheets, there being also means provided for ensuring that the superposed sheets do not become or remain stuck together in face-to-face manner but instead are kept somewhat separated in areas thereof so as to permit passage of liquid between the sheets. One means for ensuring avoidance of face-to-face sticking is to biaxially orient one sheet, having the other sheet in normal relaxed condition, and then heat the superposed sheets so as to engender crinkling or irregularities which prevent face-to-face contact of opposed walls within the tube or within the bag. Another means for avoiding such face-to-face contact is to include between the sheets in the non-welded areas a form of non-continuous spacing structure. One example of a suitable material to achieve this is a plastics mesh located between the sheets. One could instead include a microperforated film between the non-welded areas of the sheets.

Referring now to FIGS. 1 and 2, one embodiment of liquid drainage bag according to the invention is formed by welding together two superposed sheets 20, 22 by a single weld 24. One of these sheets is biaxially oriented, so that it shrinks when subjected to heat. The weld 24 is of complex shape and has a first portion 24a which largely encircles a bag volume 26, a second portion 24a which defines the external outline of a tube 28, a third portion 24c which forms a rounded end of the tube 28, and a fourth portion 24d which forms the internal outline of the tube 28 and which runs alongside and adjacent to the weld portion 24a, these portions 24d and 24a having between them a line of perforations 30. At one end of the radially inner weld portion 24a there is a loop weld 24f, the line of perforations 30 (or other line of weakening enabling the tube to be torn away from the bag) terminating a short distance, e.g. ½ inch or about 12 mm., short of the loop 24f. The weld 24 joins the superposed sheets. In use, the tube 28 is torn away from the bag volume 26 by grasping the end 24c and pulling it away from the bag volume, so starting and then continuing a tear along the line of weakening which preferably is a line of perforations 30. To strengthen the plastics material in the area where the tear starts, an extra loop of weld 24e is provided. Alternatively, a strengthening patch, e.g. of plastics material, may be applied to reinforce this area. For strengthening purposes, the extra loop weld 24f is provided in the region which will be the end of the tear, that is, the region where the tube 28 is connected to the bag volume. If desired, though this is not essential to the invention, a spigot 33, FIG. 1, may be attached to one of the superposed sheets to provide an entry to the tube 28 and an outlet spigot 34 (FIGS. 1 and 2) may be attached to said sheet at a suitable location on the bag, to provide for exit of collected liquid. An advantage of this version of the invention is that by placing the flat surfaces (e.g. 36) of the spigots upwards in suitable recesses in a weld tool, then overlaying the first sheet 22 so as to weld the flanges of the inlet and outlet spigots thereto and then overlaying the second sheet 20 and preforming the outline welds to form the peripheral bag weld in one flat weld process. One may use plastics heat welding, RF welding or impulse heat welding with the latter being currently preferred. As seen at 38 (FIG. 1), four conventional "3 ring" welds may be provided in the same operation, the centres being punched out, so that the bag can be hung up on suitable hooks for e.g. urine night drainage use. The positions of these 3-ring welds may be varied as may be needed to ensure the bag hangs in the desired orientation.

As seen in FIG. 2, according to a variation of this embodiment of the invention, a micro-perforated plastics film 44 may be heat-welded into the bag defined by the two sheets 20 and 22. This film 44 serves to assist in separating layers 22 and 20, and is optional. The film 44 may be heat welded in the same operation that produces welds 24a to 24f.

FIG. 3 is a diagram illustrating a possible shape and arrangement of combinations of bag and tube so that a plurality of such combinations can be made from a pair of superposed plastics sheets 50 and 52. These would, in use, be fed intermittently through a welding station, not shown. In their embodiment, the bag volumes 54 are substantially rectangular and the tubes 56 extend linearly from a region of the bag volume which will be the top in use. Locations of outlet spigots are indicated at 58. An alternative arrangement is shown at 64 in the lower part of FIG. 3, the bag volume being 66 and the tube 68. Other arrangements are possible and will occur to a man skilled in the art.

In accordance with the presently-preferred embodiment of the invention, a bag and tube combination is made in one welding operation by employing two superposed sheets of a heat-shrinkable plastics film, e.g. of thickness about 0.15 to 0.20 mm (0.006 to 0.008 inches). The area of the films which will constitute the bag is protected from impingement thereon of hot air by an insulating board whose size and shape substantially correspond with that of the bag portion when the latter is laid flat, this being the preferred configuration for manufacture. The area which will constitute the tube is exposed to a downward stream of hot air, e.g. at 110° to 150° C. It is found that this causes the tube portion to bend or "curl" upwardly, as illustrated in FIG. 4. This Figure shows a bag-tube combination having superposed sheets 22, 20 defining a bag volume 26 and a tubular conduit 28, welds being shown at 24a and b and an insulating board at 46. Hot air is supplied by blowers 48. It is believed, though the Inventors would not wish to be bound by this theory, that the impingement of the hot air firstly on the sheet 20 causes this film to shrink to a greater extent, and more quickly, than the underlying sheet 22. As a result, the illustrated upward curl occurs.

One advantage of this embodiment of the invention is that, since the two films 20, 22 are of the same material, any scrap is suitable for immediate recycling.

What is claimed is:

1. A bag for containing liquid comprising a pair of superimposed plastic sheets joined by a weld to form a bag, said sheets being formed so as to reduce their ability to stick together, said weld outlining in part a shape defining a tube about a periphery of said bag, said tube having an inlet for receiving fluid and an outlet for dispensing fluid into a portion of said bag, said weld including a line of weakening for permitting separation of a portion of said tube from said bag along said line of weakening while maintaining fluid communication between said tube and said bag portion.

2. The bag of claim 1 further comprising a first strengthening patch on said bag near said tube inlet for reinforcing said line of weakening and reducing puncturing of said bag when said tube is separated from a portion of said bag along said line of weakening.

3. The bag of claim 2 further comprising a microperforated film between said sheets to aid in reducing their ability to stick together.

4. The bag of claim 1 wherein said first strengthening patch includes a loop of weld.

5. The bag of claim 1 further comprising a second reinforcing patch on said bag near said tube outlet for reinforcing said line of weakening and reducing puncturing of said bag when said tube is separated from a portion of said bag along said line of weakening.

6. The bag of claim 5 wherein said second strengthening patch includes a loop of weld.

7. The bag of claim 1 further comprising at least one ring weld having a removable center to permit hanging of said bag through said ring weld.

\* \* \* \* \*